United States Patent [19]
Johnson et al.

[11] Patent Number: 5,147,349
[45] Date of Patent: Sep. 15, 1992

[54] DIODE LASER DEVICE FOR PHOTOCOAGULATION OF THE RETINA

[75] Inventors: Robert W. Johnson, Los Altos; Ralph B. Bettman, Mountain View; Acle V. Hicks, Cupertino; Michael Yessik, San Francisco, all of Calif.

[73] Assignee: Spectra-Physics, Inc., Wilmington, Del.

[21] Appl. No.: 254,994

[22] Filed: Oct. 7, 1988

[51] Int. Cl.⁵ ............................................. A61B 17/32
[52] U.S. Cl. .................................... 606/4; 606/15; 606/17
[58] Field of Search .......................... 128/395–398; 606/13–17, 4

[56] References Cited
U.S. PATENT DOCUMENTS

| | | | |
|---|---|---|---|
| 4,470,414 | 9/1984 | Imagawa et al. | 128/303.1 |
| 4,499,897 | 2/1985 | Roussel | 128/303.1 |
| 4,503,854 | 3/1985 | Jako | 128/395 |
| 4,561,436 | 12/1985 | Munnerlyn | 128/395 |
| 4,633,866 | 1/1987 | Peyman et al. | 128/395 |
| 4,672,969 | 6/1987 | Dew | 128/397 |
| 4,686,979 | 8/1987 | Gruen et al. | 128/303.1 |
| 4,719,912 | 1/1988 | Weinberg | 128/395 |
| 4,724,835 | 2/1988 | Liss et al. | 128/303.1 |
| 4,732,448 | 3/1988 | Goldenberg | 606/16 |
| 4,742,235 | 5/1988 | Koji | 128/395 |
| 4,818,660 | 3/1989 | Swartz et al. | 235/472 |
| 4,865,029 | 9/1989 | Pankratov et al. | 128/398 |

FOREIGN PATENT DOCUMENTS

| | | |
|---|---|---|
| 0131768 | 1/1986 | European Pat. Off. . |
| 0194856 | 6/1987 | European Pat. Off. . |
| 0248520 | 12/1987 | European Pat. Off. . |
| 0281161 | 7/1988 | European Pat. Off. . |
| 2599961 | 12/1987 | France . |

OTHER PUBLICATIONS

"Basics of Argon-Krypton Coagulator," Jan. 1973, pp. 205–208.
Thomas F. Deutsch et al., abstract of "Semiconductor-laser endophotocoagulation of the retina," Jun. 11, 1986, pp. 150–151.

Primary Examiner—Max Hindenburg

[57] ABSTRACT

A diode laser device and method of use for achieving transcutaneous laser photocoagulation of the retina is described. A diode laser is used since it is much more efficient than the ion or dye lasers presently used for laser photocoagulation, and therefore will not require forced air of water cooling and can be made for compact. In addition, the diode laser can be used with standard 110 v wall sockets, and does not require the high power, three phase sockets required for the ion lasers. The end result is that compared to the ion laser device, the diode laser device can be brought directly into the operating room, which makes it ideal for transcutaneous delivery.

A characteristic of diode lasers is that the emitted light diverges rapidly. In addition, the diode laser beam is emitted from a rectangular edge of a diode, and the light emitted along the longer sides of the rectangular edge will diverge more rapidly than that light emitted along the shorter sides of the rectangular edge. As a result, the emitted beam will become shaped as an ellipse as it travels from the rectangular edge.

In one embodiment of the invention, the elliptical laser beam is shaped into a circle by an optical system before it is coupled to the fiber optic cable of the delivery system. In another embodiment, the fiber optic cable is directly coupled to the rectangular edge of the diode, making the optical system for shaping unnecessary.

26 Claims, 3 Drawing Sheets

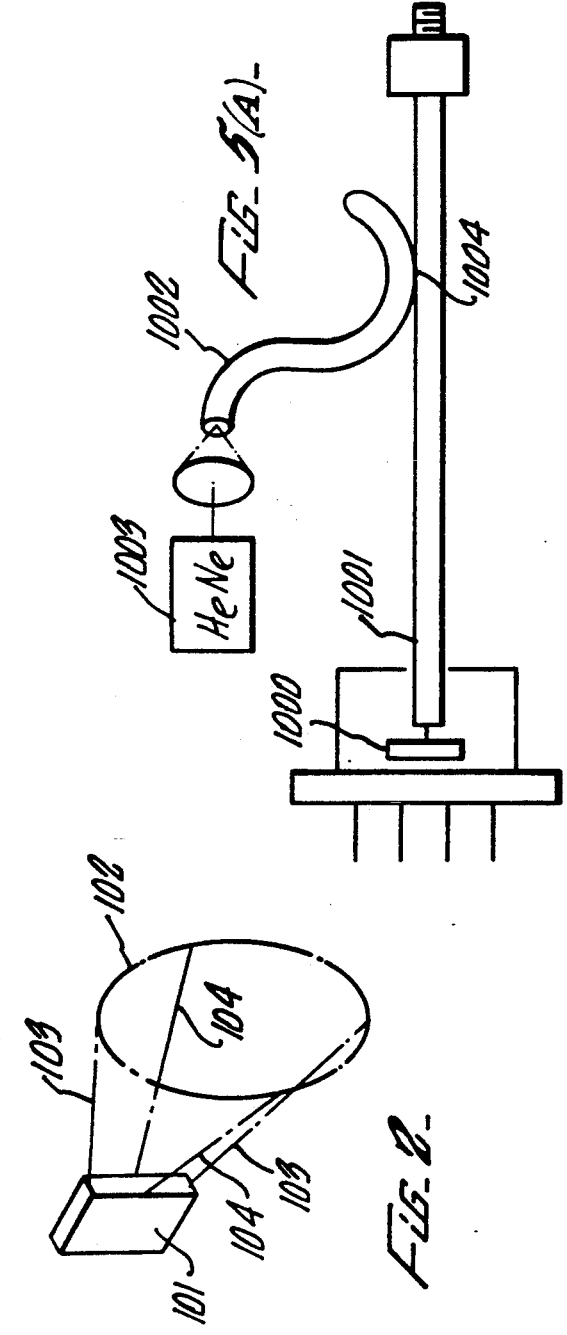
FIG. 3
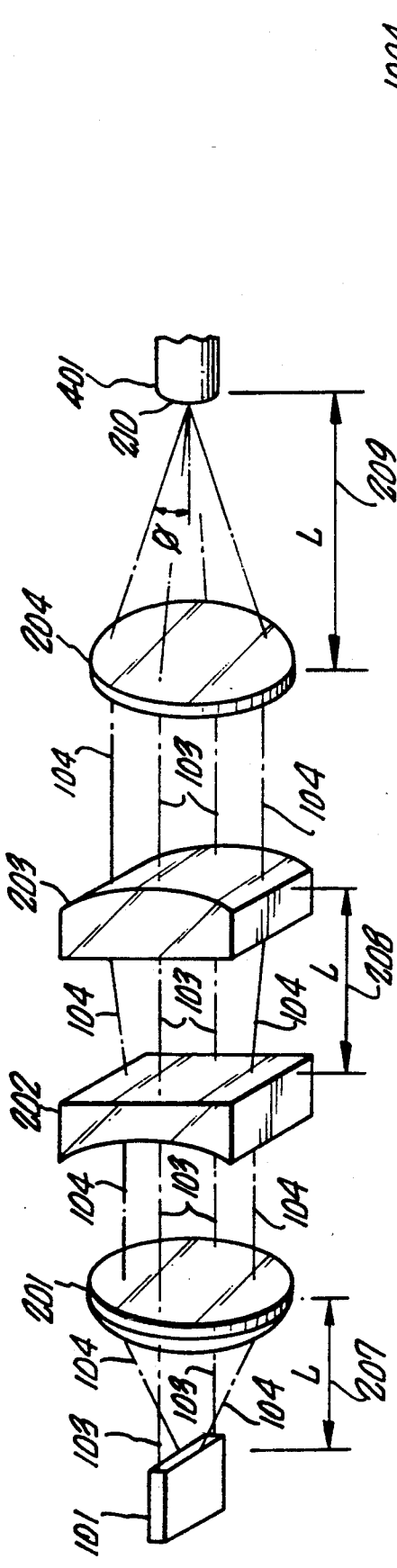
FIG. 2
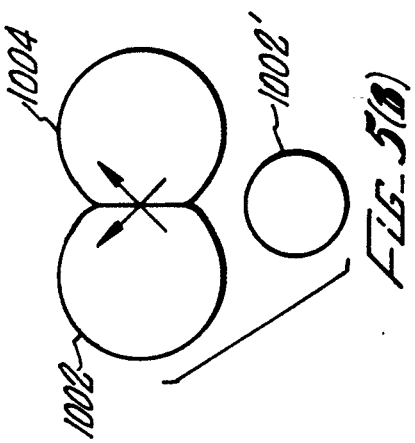
FIG. 5(A)
FIG. 5(B)

DIODE LASER DEVICE FOR PHOTOCOAGULATION OF THE RETINA

BACKGROUND OF THE INVENTION

1. Field of the Invention

This invention relates generally to a device for achieving transcutaneous laser photocoagulation of the retina, and more specifically, to a device which employs a high efficiency diode laser having a wavelength which is absorbed by the retinal pigment epithelium, enabling the device to be compact, portable, and used directly in the operating room.

2. Background of the Invention

As is known, human beings suffer from diseases, such as diabetes, which abnormally produce cells in the retinal pigment epithelium of the eye. These cells, after they are produced, will demand oxygen in order to survive, and the body will form new blood vessels in the eye to supply the newly-formed cells with oxygen. This process is known as neovascularization.

A problem is that the newly-formed blood vessels will, if their growth is left unchecked, damage the visible receptors in the retina, and the patient may lose sight. As a result, the medical profession and the laser industry collaboratively developed a technique called laser photocoagulation for checking the growth of the blood vessels.

Photocoagulation is simply the process of irradiating cells with laser light at a specific wavelength which is absorbed by the cells, causing a material in the cells to coagulate, and resulting in their ultimate death.

To destroy the blood vessels, the art developed a device employing an ion or dye laser for achieving photocoagulation. An ion or dye laser was chosen because the lasing materials used in such a laser, typically argon, krypton, or a dye, will have a wavelength which is absorbed by the hemoglobin in the blood of the blood vessel cells, causing the hemoglobin to coagulate, and the blood vessels to shrivel up and die. For example, an argon laser will produce laser light having a wavelength of either 488 nanometers (hereinafter "nm") or 514 nm, a krypton laser will produce laser light having a wavelength of 648 nm, and dye lasers will produce laser light having a wavelength range of 550–650 nm. Laser light having wavelengths approximately below 600 nm will be absorbed by the hemoglobin.

This device had then, and has now a significant number of problems, however. The predominant problem is that an ion laser is very inefficient, and the laser must be operated from a high voltage, three-phase outlet in order for it to produce laser light having enough intensity to achieve photocoagulation. Ion lasers, for example, have an efficiency level in the range of 0.1–2%, which means that only 0.1–0.2% of the input power is converted to useable laser light. To dissipate the heat which builds up from that portion of the input power which is not converted to useable laser light, a water or forced air coolant system must typically be added to the device. This results in the device being large and bulky, because of the coolant system which is required, and a device which is not portable, because it must be coupled to a special, high voltage, three-phase outlet in order to get the necessary input power. Moreover, because of its size, and lack of portability, the device cannot easily be brought into an operating room, making the use of this device in conjunction with retinal eye surgery inconvenient.

Another problem is that the device acts to suppress the growth of the blood vessel cells only, and does not act at all on the abnormal cells whose oxygen requirements results in the growth of the blood vessel cells in the first instance. As a result, after a particular treatment with the device is performed resulting in the clearing away of the blood vessels, the oxygen demands of the abnormal cells will still continue, and the body will respond by growing more blood vessel cells, necessitating additional treatments with the device.

Another problem is that the available options for delivering the light to the retina are somewhat limited. There are presently two known ways of delivering laser light to the retina: transpupilary and transcutaneous.

In the transpupilary method of delivery, laser light is delivered to the retina through the pupil, without requiring an incision in the eye. In the transcutaneous method of delivery, on the other hand, a cut is made in the eye, and a device known as an endoprobe is inserted, and used to deliver the laser light to the retina. The transcutaneous method of delivery is particularly advantageous when an incision has already been made in the eye in the course of eye surgery. In a surgery procedure known as a vitrectomy, for example, strands of solid material which have formed in the vitreous material between the lens and the retina are cut away, since otherwise, the strands may affect the vision and hurt the retina. During the course of a vitrectomy, it is a simple matter to insert an endoprobe in the incisions already made in order to photocoagulate portions of the retina. Since the ion laser device, as discussed above, cannot easily be brought into the operating room, it is difficult to use the transcutaneous method of delivery with the device.

Diode lasers have wavelengths which will be absorbed, and hence coagulate the retinal pigment epithelium cells, and destroy adjacent abnormal retinal cells. Krypton and long-wavelength dye lasers also are absorbed by the pigment cells. However, commonly available wavelengths are in the infrared portion of the light spectrum, i.e. in the range of 700–840 nm, which are not highly visible. As a result, it is difficult to position diode laser beams at the specific spot on the retina to be photocoagulated. The light produced by ion lasers, on the other hand, is visible, making it a relatively simple matter to track and position the laser beam. The result is that the art is and was discouraged from using, and did not in fact use, diode lasers for achieving photocoagulation. This is in spite of the fact that the use of such lasers would have had enormous beneficial consequences in that they could be used to destroy the abnormal retinal cells instead of just the problematic blood vessel cells, making further treatments unnecessary. In addition, krypton and long-wavelength dye lasers were available for this purpose.

Accordingly, it is an object of the present invention to provide a device for achieving transcutaneous laser photocoagulation of the retina which is compact, portable, and can be used in an operating room, and which achieves photocoagulation of the abnormal retinal cells through the use of laser light which is absorbed by adjacent pigment epithelium cells, and which provides a means for visibly tracking and positioning the laser beam onto the specific portion of the retina to be photocoagulated.

SUMMARY OF THE INVENTION

To achieve the foregoing objects, and in accordance with the purpose of the invention as embodied and broadly described herein, there is provided a diode laser device for achieving transcutaneous laser photocoagulation of abnormal retinal cells which is compact, portable, and useable directly in an operating room, which has a wavelength which is absorbed by adjacent pigment epithelium cells, and which has means for visibly locating and tracking the position of the beam on the retina.

An exemplary embodiment comprises a diode laser having a wavelength in the range of 700–840 nm which produces an elliptical laser beam, an optical system which is coupled to the laser to first circularly shape the elliptical laser beam and merge the circularly shaped light with a visible aiming beam produced by another light source, such as a helium-neon (He-Ne) laser or a light-emitting diode. The optical system then couples the merged beam to a fiber optical cable for ultimate delivery to a patient's retina through an endoprobe. Because of the presence of the visible, aiming beam, the position of the merged beam on the retina will be visible, enabling the merged beam to be easily situated at the location of the retina which is to be photocoagulated.

An alternative embodiment comprises eliminating the optical system entirely, and directly coupling a first fiber optic cable at one end directly to the diode of the diode laser. The other end is coupled to an endoprobe for delivering the light to the retina. The visible aiming beam is then coupled to a second fiber optical cable at one end having a much smaller diameter than the first fiber optical cable, and the other end is then coupled to an intermediate position on the first cable, enabling the visible beam and diode laser beam to merge. The diameter of the second cable is chosen to be much smaller than the diameter of the first cable in order to eliminate losses of the diode beam, which would otherwise occur if the diameters were approximately equal. In the embodiment, the diameter of the first cable is 200 microns, while the diameter of the second cable is 6 microns.

Another alternative embodiment comprises eliminating portions of the optical system and the visible aiming beam, and using a diode laser having a diode which produces laser light having a wavelength in the range of 600–700 nm, typically 685 nm or less. These wavelengths are short enough so that the light will be more visible, but will also be high enough so that the light will still be absorbed by the retinal pigment epithelium cells. The diode laser beam can either be directly coupled to a fiber optic cable attached to an endoprobe, in which case the entire optical system can be eliminated, or the laser beam can first be circularly shaped before being coupled to the fiber optic cable, in which case portions of the optical system must be retained.

Another alternative embodiment comprises using a diode laser having a laser diode which is combined with a visible light-emitting-diode (hereinafter "LED") on the same chip. The beam produced by the chip will be a merged laser diode beam and visible beam, which can be directly coupled to a fiber optic cable, bypassing and eliminating the need for an optical system for merging and shaping the beams. Of course, the merged beam can first be shaped before coupling to a fiber optic cable, in which case portions of the optical system must be retained.

Another embodiment comprises not merging the diode laser beam with a visible beam at all, but simply positioning the beam indirectly by positioning the endoprobe over the spot on the retina which is to be photocoagulated.

BRIEF DESCRIPTION OF THE DRAWINGS

FIG. 2 is a diagram of a laser diode of a diode laser;

FIG. 3 shows a more detailed block diagram of the optical system of the exemplary embodiment of FIG. 1;

FIG. 5(A) is a diagram of the interface between two fiber optic cables; and

FIG. 5(B) is a diagram of another exemplary embodiment of the subject invention.

DESCRIPTION OF THE PREFERRED EMBODIMENT

Figure 1:
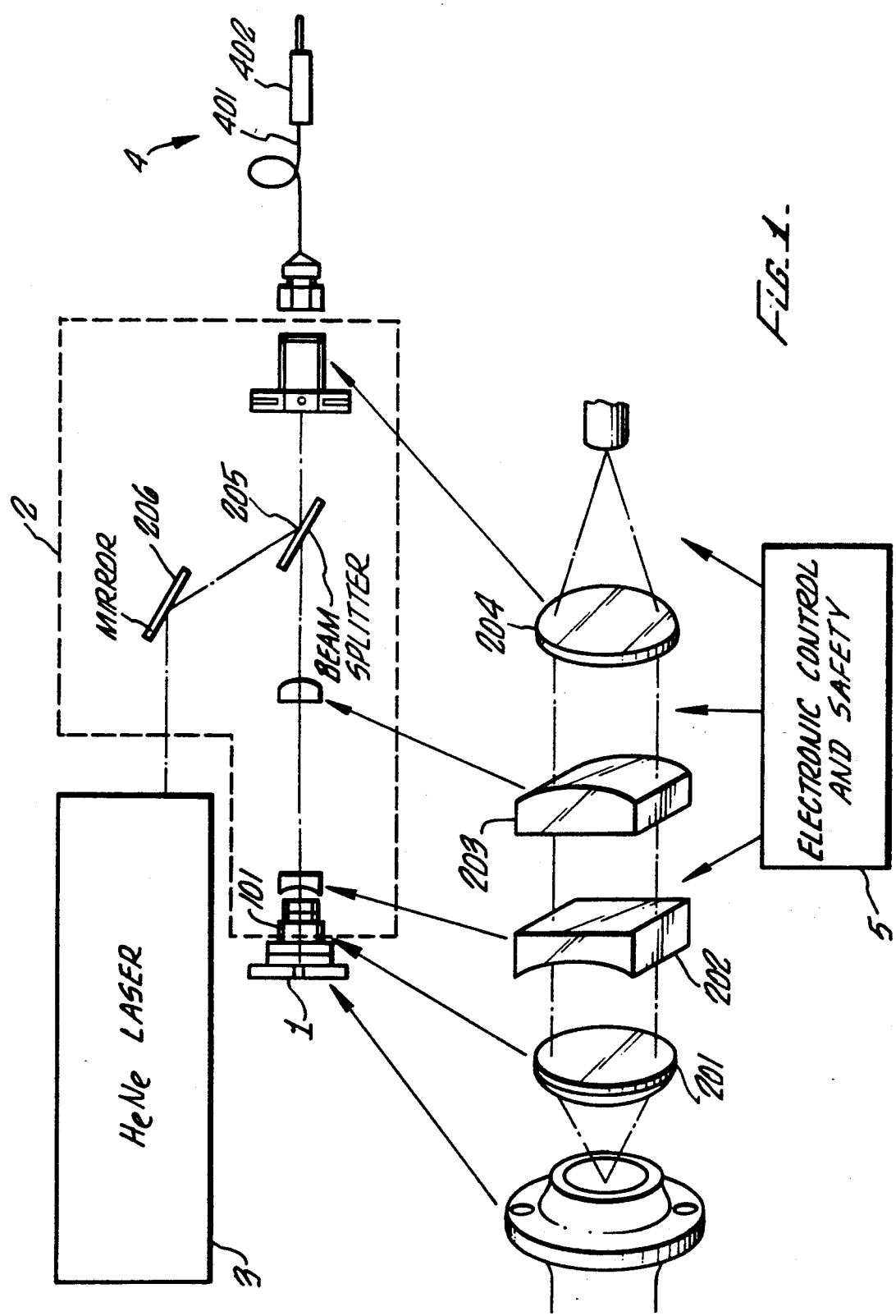
FIG. 1 shows a block diagram of an exemplary embodiment of the subject invention.

An exemplary embodiment of the subject invention as shown in FIG. 1. As illustrated in the Figure, the embodiment comprises diode laser 1, optical system 2, visible light source 3, delivery system 4, and electronic control and safety system 5. The diode laser and the visible light source are both coupled to the optical system. The diode laser has laser diode 101 which produces a diode laser beam, and the visible light source produces a visible aiming beam. The diode laser beam is first shaped by the optical system, which then merges it with the visible aiming beam, and couples the merged beam to the delivery system.

The delivery system, as shown in the Figure, comprises fiber optical cable 401 and endoprobe 402. As illustrated, the fiber optic cable is coupled to the optical system at one end, and is coupled to the endoprobe at the other end. The merged beam from the optical system is transmitted through the delivery system for ultimate delivery to a patient's retina.

Electronic control and safety system 5 is coupled to all the other systems of the device. It both enables an operator to select a certain mode of operation, and power and timing parameters such as pulse width, energy level, and it also contains certain safety features.

In the embodiment of FIG. 1, the laser diode is either a Sony Model 303 WT, or a Spectra-Diode Labs Model 2431 H1. In fact, any diode can be used which produces laser light having a wavelength in the range of 700–840 nm. Since these diodes are so efficient, they only require current in the range of 1 ampere at a few volts to operate.

In the embodiment of FIG. 1, the visible light source is a He-Ne laser, and the endoprobe is a Cooper Vision Laser Endoprobe (20 GA), Cat. No. 0101-0339. In fact, any visible light source will suffice that can be coupled through an optical fiber.

A more detailed diagram of diode 101 in the embodiment of FIG. 1 is illustrated in FIG. 2. As illustrated, the diode will emit a laser beam 102 from its rectangular end. The circumference of the beam of emitted light has two groups of component rays 103 and 104, which are respectively emitted from the short and long sides of the rectangular edge of the diode, and which will diverge at different speeds, with the result that the emitted light will form an ellipse as it travels from the diode. Rays 104 will diverge at a faster rate than rays 103. Fiber optic cable 401, on the other hand, is circular in shape at the ends, and it will be necessary to shape the emitted light into a circle before it can be effectively coupled to the fiber optic cable without significant losses of the emitted light. This is one of the functions of optical system 2.

A detailed diagram of optical system 2 of the embodiment of FIG. 1 is illustrated in FIG. 3. The reference numbers in FIG. 3 are identical to those in FIG. 1. As illustrated, the system comprises collimating lens 201, cylindrical lenses 202 and 203, and coupling lens 204. The system also comprises polarizing beam splitter 205, and mirror 206, but these elements are only included in FIG. 1, not FIG. 3. Also shown in the Figure are diode 101, rays 103 and 104, and one end of fiber optic cable 401.

As illustrated, the optical system will affect rays 103 and 104 differently. Rays 103 will be collimated, that is straightened by collimating lens 201, and will then pass through cylindrical lenses 202 and 203 substantially unaffected. Coupling lens 204 will then focus rays 103 to an area approximately 200 microns in diameter.

Rays 104 will also be collimated by collimating lens 202. Cylindrical lenses 202 and 203 in combination act as an up-collimator, that is, they increase the spacing between rays 104 to equalize it with the spacing between rays 103. As illustrated in FIG. 2, the spacing is different because of the rectangular geometry of the edge of the diode. Lens 202 is a plano-concave lens, which causes the rays to diverge a certain amount, while lens 203 is a corresponding plano-convex lens, which causes the rays to converge sufficiently so they are collimated, i.e. straight, again. As with rays 103, coupling lens 204 focuses the rays to an area having a diameter of approximately 200 microns. The net result is that beam 102 has been shaped into a circle having a diameter of 200 microns by the optical system.

In the embodiment of FIG. 3, collimating lens 201 is a spherical lens having an f-number, which as is known in the art, is the ratio of the focal length of the lens to the diameter of the lens, of 1.0, although a lens having an f-number of any value less than one will suffice.

Cylindrical lens 202 is a plano convex lens having a focal length of 60 centimeters (hereinafter "cm"), and cylindrical lens 203 is a plano convex lens having a focal length of −25 cm. As indicated earlier, the cylindrical lenses in combination act as an up-collimator, that is, they expand the spacing between rays 104 so that it equals the spacing between rays 103. In the embodiment of FIGS. 1–3, the spacing between rays 103, at least initially, is 160 microns, and this is approximately 2½ times the initial spacing between rays 104. Therefore, any combination of cylindrical lenses will work in the embodiment of FIGS. 1–3 as long as the collimation ratio of the two lenses, which is defined as the ratio of the absolute values of the focal length of lens 202 to that of lens 203, is approximately equal to the ratio of the spacing between rays 103 to the spacing between rays 104. As mentioned earlier, in the case of the embodiment of FIGS. 1–3, the ratio of the spacing, which is determined by the geometry of the edge of the diode, is approximately 2½. The collimation ratio for the embodiment of FIG. 3 is 60/25, or 2.4. If the dimensions of the edge of the diode were changed however, the collimation ratio of lenses 202 and 203 should correspondingly be changed.

The distance between the edge of diode 101 and collimating lens 201, indicated as 207 in FIG. 3, is also important. It should be equal to the focal length of lens 201, which in the embodiment of FIGS. 1–3, is 4.5 millimeters (hereinafter "mm"). If the focal length of lens 201 is changed, the distance 207 between the diode and the lens should correspondingly be changed. However, the distance and hence focal length should not be too large, as this will require a larger diameter collimating lenses, which can be expensive.

The distance between the two cylindrical lenses of the up-collimator, that is lenses 202 and 203, indicated as 208 in FIG. 3, should be equal to the difference between the absolute values of the focal lengths of lens 202 and lens 203, which in the embodiment of FIG. 3, is 35 cm.

The distance between the coupling lens and the end of the fiber optic cable, indicated as 209 in FIG. 3, should be equal to the focal length of coupling lens 204.

The focal length of the coupling lens is an important parameter, and depends on the size and numerical aperture of the fiber optical cable for which the lens is acting as a coupler. As is known, the numerical aperture is a measure of an angle known the critical angle. The critical angle is defined with respect to normal incidence at the face of the end of the fiber optic cable. The angle of incidence of light which is incident upon the face of the end of the cable must be less than the critical angle in order to minimize reflective losses. In FIG. 3, for example, the incident light makes an angle of incidence $\theta$ at face 210 of the end of the fiber optic cable 401. This angle must be below the critical angle, $\theta c$, associated with the fiber optic cable. As is known, the numerical aperture, N/A, is defined as the sine of one half of the critical angle. In other words: $N/A = \sin \frac{1}{2}\theta c$. The focal length must be chosen so that both the diameter of the focused beam at the face 210 of the fiber optic cable is less than or equal to the diameter of the fiber optic cable, and the angle of incidence of the beam is less than the critical angle of the cable. In the embodiment of FIG. 3, the focal length of lens 204, and hence the distance 209, must be chosen so that the angle of incidence is below the critical angle of fiber optic cable 401.

In the embodiment of FIG. 3, the focal length of lens 204, and hence distance 209, is 15 mm. In addition, the diameter of the fiber optic cable is 200 microns, and the numerical aperture of the cable is 0.23. However, the diameter of the cable can be any value between 100–300 microns, and if changed from 200 microns, the focal length of coupling lens 204 should correspondingly be changed. A larger diameter is possible, but is not recommended, since it may lower the power density of the laser beam which is delivered to the patient's retina to the extent that photocoagulation is not achieved.

The end result of the optical system of FIG. 3 is that the optical system produces a beam of diode laser light having a diameter, 200 microns, approximately equal to the length of the rectangular edge of the diode, 160 microns. In other words, a magnification of approximately unity in this dimension is achieved.

Besides its beam shaping function, the optical system of FIG. 3 also merges the diode laser beam with the visible aiming beam. The merging takes places at the polarizing beam splitter, which passes all linearly polarized light having a first polarization, but reflects all linearly polarized light having a second polarization which is rotated 90° from the first polarization. The beam-splitter has a first surface and a second surface, and mirror 406 directs the visible aiming beam to a particular point on the first surface of polarizing beam splitter 405. In addition, the polarizing beam splitter is situated such that the diode laser beam impinges upon the second surface of the beam splitter.

The visible laser aiming beam will be linearly polarized in the second direction, and hence reflect from the first surface of the beam splitter. Moreover, the diode laser beam from the diode laser will be linearly polarized in the first direction and will transmit through the beam splitter and emerge at the second surface at the same point where the visible beam reflects. The result is that the diode laser beam and the visible aiming beam merge before impinging upon the coupling lens, and the merged beam is coupled to and transmitted through the delivery system to the patient's retina.

Not shown in FIG. 3 is a liquid crystal shutter for adjusting the intensity of the aiming beam. The shutter comprises a liquid crystal followed by a sheet polarizer and is placed in the path of the visible aiming beam before it strikes the beam-splitter. As is known, the liquid crystal will rotate the polarization of the visible aiming beam depending on the voltage applied to it, while the sheet polarizer will act as a polarization filter for light of a particular polarization. The visible aiming beam will already be linearly polarized, and the liquid crystal will rotate the polarization depending on the voltage applied, so that the degree to which the light is filtered by the sheet polarizer will change. The result is that the intensity of the aiming beam can be adjusted by varying the voltage applied to the liquid crystal.

The electronic control and safety system performs two functions. First, it allows an operator to control the mode of operation, and also the power and timing characteristics of the diode laser light which is delivered to the retina. Second, it provides a safety shutter for shutting off the diode laser beam when certain conditions are met. Regarding the control aspects, the system provides the following switches or controls:

select operating mode, i.e. continuous, repeat pulse, or single pulse mode
select laser power
select pulse width
select time between pulses in repeat pulse mode
adjustment in visible aiming beam intensity
counter for number of pulses delivered
a counter reset button
a "READY" button
a foot switch.

The select mode switch enables an operator to deliver a continuous beam, a series of pulses, or a single pulse to the patient's retina. The power switch enables the operator to select the power delivered. The switch should enable the operator to select between 0.1-1 watts, which range is sufficient to achieve photocoagulation of abnormal retinal cells without affecting surrounding healthy tissue.

The pulse width switch enables the operator to select the width of a single pulse. The switch should enable the operator to select a width of between 50 milliseconds (hereafter "msec") and 5 sec.

The time between pulses is a parameter which depends on the treatment to be given to a particular patient, and any adjustment in aiming beam intensity is done simply for the convenience of the operator in locating and positioning the beam. The counter counts the number of pulses applied in repeat pulse mode, and the counter reset button simply resets the counter.

The "READY" button is a safety feature and is used to control the safety shutter, which in FIG. 3, is placed between coupling lens 204 and end face 210 of fiber optic cable 401. Before the "READY" button is pushed, the safety shutter will block the diode laser beam, and prevent it from exiting the device to the delivery system. When the button is pushed, the shutter opens.

The foot switch is then used to control delivery of the diode laser light to the patient. When the foot switch is depressed, the light will be delivered according to the selected operating mode, and at the selected power level. If continuous mode is selected, the light will be delivered continuously. If single pulse mode is selected, a single pulse of light will be delivered at the selected single pulse width. If repeat pulse mode is selected, a pulse train will be delivered for as long as the switch is depressed, having a single pulse width and time between pulses as selected by the operator.

Sensing means are also provided for sensing whether the fiber optical cable of the delivery system is attached to the device. If not, the sensing means causes the shutter to close, thereby preventing any diode laser light from accidentally being emitted from the device.

In addition, feedback loop means are also provided for adjusting the current which flows through the diode until the selected output power of the diode laser light is achieved. This is to take account of changes in the current required to achieve a certain output power which may occur, for example, as the laser ages. The feedback loop means compares the actual output power level with the selected output power level, and adjusts the input current until the two are equal.

Figure 4:
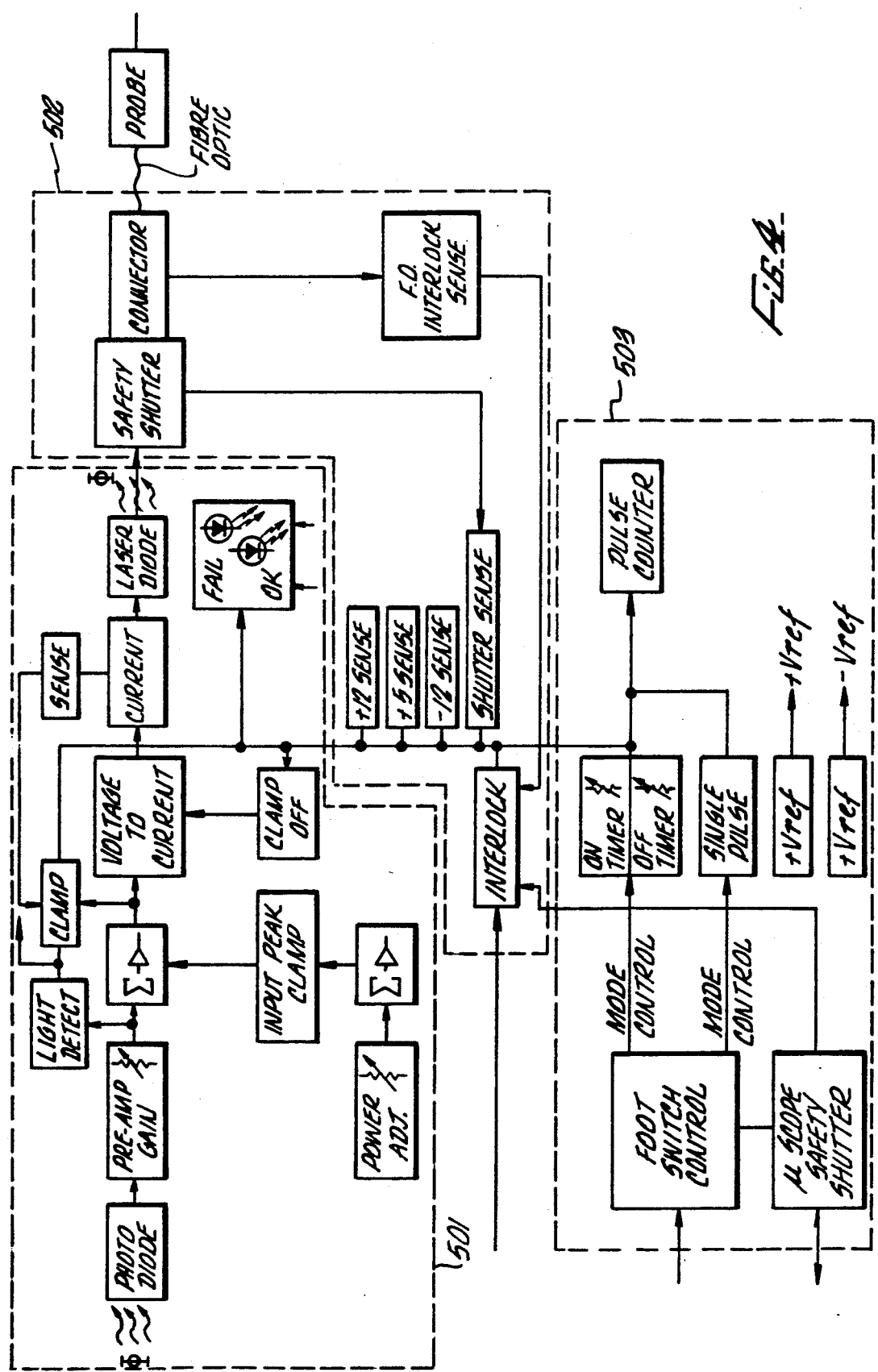
FIG. 4 is a block diagram of the electrical safety and control system of the exemplary embodiment of FIG. 1.

A diagram of the electronic control and safety system is shown in FIG. 4. As shown in the Figure, the system comprises feedback loop means 501, safety means 502, and control means 503. As discussed above, the feedback loop means is coupled to the diode laser, and ensures that enough current is applied to the laser diode to achieve the selected output power. The safety means comprises a safety shutter which is placed between the coupling leans and the fiber optic connector. The safety shutter is coupled to an interlock sensor, which senses whether or not the delivery system is attached to the device. If not, the sensor causes the safety shutter to close. Finally, the control means are coupled to all the other components of the system. As mentioned earlier, the control means provides a capability for selecting operating mode, output power, pulse width, time between pulses, a "READY" button for opening the shutter and activating the foot switch, and a foot switch for controlling the delivery of the laser light.

To operate the device, an operator first selects the mode, pulse width, output power, and time between pulses. Since the "READY" button has not been pushed, no diode laser light is yet delivered. The visible aiming beam, on the other hand, is always on, and delivered to the patient's retina. The operator then looks through a microscope, and positions the location of the aiming beam by moving the endoprobe until the beam is situated at that portion of the retina which is to be photocoagulated. The operator then pushes the "START" button, and depresses the foot switch to deliver the diode laser light.

An alternative embodiment comprises using a diode laser having a wavelength in the range of 600-700 nm, and typically 685 nm or less. Such a wavelength is short enough so that the light will be more visible, yet long enough so that the light will still be absorbed by the retinal cells. Since the diode laser light will be more visible, the visible light source 3, mirror 206, and beam splitter 205 can be eliminated. Of course, in this embodiment, the power of the delivered beam will have to be set low enough during the locating and positioning steps so that photocoagulation of the retina will not occur, and then stepped up to a higher level after the beam has been properly positioned, when it is desired to photocoagulate the retina. Another control can be added to the device for this purpose. It is possible to directly couple fiber optic cable 401 to diode 101, and eliminate the remaining portion of the optical system used to shape the beam. Alternatively, this portion of the optical system can be left in place, to shape the laser beam, and couple it to the cable. In this case, the only step which is eliminated in the step of merging the beam with a visible, aiming beam.

A second alternative embodiment comprises using a laser diode which is combined with a visible LED on the same chip. This would also eliminate the necessity of a visible light source, and associated mirror and beam splitter for merging, since the diode laser would already produce a merged beam. As before, in this embodiment, the chip could be coupled directly to the fiber optic cable, or shaped by the optical system, and then coupled to the cable.

A third alternative embodiment comprises locating and positioning the diode laser merely by visually positioning the endoprobe at the spot on the retina to be photocoagulated. As a result, the visible light source and associated optical elements for merging can be eliminated. As above, the laser beam can be directly coupled, or shaped before being coupled to the cable.

In all the above embodiments, to directly couple the beam to the cable, it is only necessary to place the end of the cable in close proximity to the diode, and ensure that the diameter of the cable be greater than the length of the long rectangular edge of the diode. For example, if the diode edge is 160 microns, a fiber optic cable diameter of 200 microns can be used. Alternatively, the shape of the cable can be changed so it is elliptical, and matches the shape of the diode edge.

A fourth embodiment comprises directly coupling the diode laser beam to an edge of a first fiber optic cable which is coupled to an endoprobe at the other end for delivery. In addition, the visible aiming beam is directly coupled to a second fiber optic cable at one end, and the other end is directly coupled to an intermediate point of the first cable. In this embodiment, the entire optical system, both merging and shaping components, can be eliminated.

As illustrated in FIG. 5(A), this embodiment comprises directly coupling one end of a first fiber optic cable 1001 to laser diode 1000, directly coupling one end of a second fiber optic cable 1002 to visible light source 1003, and then coupling the other end onto an intermediate point of the first cable. The diameter of the second cable should be chosen to be substantially less than the diameter of the first cable. As illustrated in FIG. 5(B) at the interface 1001 between the two cables, there will be substantial losses of the diode laser beam, from the first cable 1004 to the second cable 1002 when the diameters are the same. However, when the diameter of the second cable 1002 is much smaller, the losses will be less.

For example, if the diameter of the first cable is 200 microns, the diameter of the second pipe can be 6 microns.

Additional advantages and modifications will readily occur to those skilled in the art. The invention in the broader aspects is not, therefore, limited to the specific details, representative methods, and illustrative examples shown and described. Accordingly, departures may be made from such details without departing from the spirit or scope of applicant's general inventive concept.

Specifically, the invention is intended to encompass all embodiments of a laser diode device for transcutaneous laser photocoagulation of the retina including embodiments where the diode laser is or is not merged with a visible aiming beam, is or is not directly coupled to a fiber optic cable, is or is not shaped before being coupled to a fiber optic cable.

What is claimed is:

1. In a device for achieving photocoagulation of the retina upon delivery of a laser beam to the retina,
   a diode laser for producing a diode laser beam from a diode within the diode laser, the beam diverging along an optical path extending from the diode into a beam having an approximately elliptical shape in cross-section; and
   an optical system configured to substantially collimate the beam, and including at least one lens matched to said beam and configured to shape the beam so that it is approximately circular in cross-section.

2. The device of claim 1 further comprising a fiber optic cable, the cable having a first end with a cross-sectional diameter, and a second end, and the cable also having a critical angle, wherein the first end of the cable is positioned at a location along the optical path, and the optical system is situated between said diode of said diode laser and said first end of said fiber optic cable, and is further configured to focus the beam such that the beam, once focused, at the location where the first end of the cable is positioned, has a cross-sectional diameter approximately less than the cross-sectional diameter of the first end of the cable, and impinges upon the first end of the cable at an incident angle approximately less than the critical angle of the cable.

3. A method for achieving diode laser photocoagulation of the retina comprising the steps of:
   providing a diode laser;
   producing a diode laser beam from a diode within the diode laser which extends along an optical path beginning at the diode;
   diverging the beam, at least partly, along the optical path after it is emitted from the diode to form a beam having an approximately elliptical shape in cross-section;
   substantially collimating the beam;
   shaping the beam utilizing at least one lens in an optical system matched to said beam and configured so that the beam is approximately circularly shaped in cross-section; and
   delivering the beam, once substantially collimated and shaped, to the retina.

4. The method of claim 3 wherein the delivering step further comprises the substeps of:
   providing a fiber optic cable having a first end which, in cross-section, has a diameter, having a second end, and having a critical angle;
   positioning the first end of the cable at a location along the optical path;
   situating said optical system between said diode of said diode laser and said first end of said cable;
   focusing the beam so that the beam, once focused, at the location where the first end of the fiber is positioned, has, in cross-section, a diameter approximately less than the diameter of the first end of the cable, and impinges upon the first end of the cable at an incident angle approximately less than the critical angle of the cable; and positioning the second end of the cable to direct the beam to the retina.

5. The method of claim 4 wherein said substep of positioning said second end comprises coupling the second end of the cable to an endoprobe, and inserting the endoprobe into the eye.

6. The device of claim 2 further comprising an endoprobe coupled to the second end of the cable.

7. A diode laser device for achieving laser photocoagulation of the retain comprising:

a diode laser for producing a diode laser beam, wherein the beam is emitted from a diode within the diode laser, and diverges, at least partly, along an optical path beginning at the diode to form a beam which, in cross-section, is approximately elliptical in shape;

a fiber optic cable having first and second ends, and a critical angle, the first end, in cross-section, having a diameter, and being situated at a location along said optical path; and an optical system positioned along the optical path and situated between said diode of said diode laser and said first end of said fiber optic cable, which is configured to substantially collimate the beam, and which includes at least one lens matched to said beam and configured to shape said beam so that it is approximately circular in cross-section, and to focus the beam such that the beam, once shaped and focused, at the location where the first end of the cable is positioned, has a cross-sectional diameter approximately less than that of the first end of the cable, and impinges upon the first end of the cable at an incident angle approximately less than the critical angle; and means for positioning the second end of the cable to deliver the beam to the retina.

8. The device of claim 6 wherein the positioning means is an endoprobe.

9. The device of claims 1 or 6 wherein said diode laser beam has a wavelength approximately within the range of 600–700 nm.

10. The device of claim 8 wherein the diode laser beam has a wavelength approximately within the range of 685 nm or less.

11. A diode laser device for achieving laser photocoagulation of the retina comprising:

a diode laser for producing a diode laser beam;

an optical system;

a fiber optic cable having first and second ends, wherein said diode laser is spaced from said first end of said fiber optic cable, and said laser beam has, in cross-section, unequal axes at said diode laser, and follows an optical path from said diode laser to a cross-sectional, outward face at the first end of said fiber optic cable, wherein said fiber optic cable has a critical angle, and said face has a diameter, wherein said optical system is situated along said optical path between said diode of said diode laser and said outward face of said first end of said fiber optic cable, and includes at least one lens matched to said beam and configured to a) shape said beam into a beam having a cross-section with substantially equal axes; and b) focus said beam into a beam at said face which has a cross-sectional diameter approximately less than said diameter of said face, and which has an angle of incidence at said face approximately less than said critical angle of said fiber optic cable; and retinal delivery means coupled to the second end of said cable.

12. The device of claim 10 wherein said optical system comprises a plano-concave cylindrical lens having a focal length, and a plano-convex cylindrical lens, also having a focal length, and spaced from said plano-concave lens by approximately the difference in absolute values between said focal lengths, wherein the lenses have a collimation ratio approximately equal to the ratio of said cross-sectional, unequal axes of said laser beam at said diode laser.

13. The device of claim 10 wherein said optical system further comprises a coupling lens having a focal length, which is spaced from said face by about said focal length, and the focal length is chosen so that said cross-sectional beam diameter at said face is approximately less than said diameter of said face, and said angle of incidence at said face is approximately less than said critical angle.

14. A method for achieving laser photocoagulation of the retina comprising:

producing a diode laser beam from a diode laser, the beam having a wavelength which is absorbed by retinal cells;

providing a fiber optic cable having first and second ends;

spacing said diode laser from said first end of said fiber optic cable, wherein said laser beam has, in cross-section, unequal axes at said diode laser;

directing said beam to follow an optical beam from said diode laser to a cross-sectional outward face at the first end of said fiber optic cable, wherein said fiber optic cable has a critical angle, and said face has a diameter;

situating an optical system between said diode laser and said outward face of said first end of said fiber optic cable;

including at least one lens in said optical system;

matching said at least one lens to said beam and configuring said at least one lens to shape said beam into a beam having a cross-section with substantially equal axes;

focusing said beam into a beam at said face which has a cross-sectional diameter approximately less than said diameter of said face, and which has an angle of incidence at said face approximately less than said critical angle of said fiber optic cable; and delivering the beam to the retina.

15. The method of claim 13 wherein the shaping step comprises the substeps of:

providing a plano-concave cylindrical lens having a focal length, and a plano-convex cylindrical lens, also having a focal length, both lenses being provided along said optical path; and spacing said plano-convex lens from said plano-concave lens by approximately the difference in absolute values between said focal lengths, wherein the lenses have a collimation ratio approximately equal to the ratio of said cross-sectional, unequal axes of said laser beam at said diode laser.

16. The method of claim 13 wherein the focusing step comprises the substeps of:

providing a coupling lens having a focal length along said optical path; and spacing said lens from said face by about said focal length, wherein the focal length is chosen so that said cross-sectional beam diameter at said face is approximately less than said diameter of said face, and said angle of incidence at said face is approximately less than said critical angle.

17. The method of claims 3 or 13 further comprising producing a diode laser beam having a wavelength approximately within the range of 600–700 nm.

18. The method of claim 16 further comprising producing a diode laser beam having a wavelength approximately within the range of 685 nm or less.

19. The device of claim 8 wherein said diode laser produces a beam having a wavelength of about 685 nm or less.

20. The method of claims 3 or 13 further comprising producing a diode laser beam having a wavelength approximately within the range of 700–840 nm.

21. The device of claims 1 or 6 wherein said diode laser produces said diode laser beam having a wavelength in the range of 700–840 nm.

22. In a device for achieving photocoagulation of the retina upon delivery of a laser beam to the retina,
  a diode laser for producing a diode laser beam from a diode within the diode laser, the beam diverging along an optical path extending from the diode into a beam having an approximately elliptical shape in cross-section;
  a fiber optic cable having first and second ends, the first end having a maximum cross-sectional extent, and being situated at a location along said optical path, and the cable also having a critical angle; and
  an optical system situated between said diode of said diode laser and said first end of said fiber optic cable, and including at least one lens matched to said beam and configured to adapt said beam such that said beam, at the location where the first end of the cable is located, has a maximum cross-sectional extent approximately smaller than the maximum cross-sectional extent of the first end, and impinges upon the first end at an angle approximately smaller than the critical angle.

23. A method for achieving diode laser photocoagulation of the retina comprising the steps of:
  providing a diode laser;
  producing a diode laser beam from a diode within the diode laser which extends along an optical path beginning at the diode;
  diverging the beam, at least partly, along the optical path after it is emitted from the diode to form a beam having an approximately elliptical shape in cross-section;
  providing a fiber optic cable having a first end which, in cross-section, has a maximum cross-sectional extent, the cable also having a critical angle;
  positioning the first end of the cable at a location along the optical path;
  situating an optical system between the diode of said diode laser and the first end of the fiber optic cable;
  including at least one lens in said optical system;
  matching said at least one lens to said beam and configuring said at least one lens to adapt the beam such that the beam, at the location where the first end of the fiber optic cable is located, has a maximum cross-sectional extent approximately smaller than the maximum cross-sectional extent of the first end of the cable, and impinges upon the first end at an angle approximately smaller than the critical angle of the cable; and
  positioning the second end of the cable to deliver the beam to the retina.

24. A diode laser device for achieving laser photocoagulation of the retina, comprising:
  a diode laser for producing a diode laser beam, wherein the beam is emitted from a diode within the diode laser, and diverges, at least partly, along an optical path beginning at the diode to form a beam which, in cross-section, is approximately elliptical in cross-section;
  a fiber optical cable having first and second ends, the first end having a maximum cross-sectional extent, and being situated at a location along the optical path, and the cable also having a critical angle;
  an optical system situated between the diode of said diode laser and the first end of the fiber optical cable, and including at least one lens matched to said beam and configured to adapt the beam such that the beam, at the location where the first end of the cable is positioned, has a maximum cross-sectional extent approximately smaller than the maximum cross-section extent of the first end of the cable, and impinges upon the first end of the cable at an angle approximately smaller than the critical angle; and
  directing means coupled to the second end of the cable for directing the beam to the retina.

25. The device of claim 23 wherein the directing means is transcutaneous directing means.

26. The device of claim 24 wherein the trancutaneous directing means is an endoprobe.

* * * * *